United States Patent [19]

Sarma et al.

[11] Patent Number: 5,419,338
[45] Date of Patent: May 30, 1995

[54] AUTONOMIC NERVOUS SYSTEM TESTING BY BI-VARIATE SPECTRAL ANALYSIS OF HEART PERIOD AND QT INTERVAL VARIABILITY

[75] Inventors: Jonnalagedda S. M. Sarma, Pasadena; Kalyanasundaram Venkataraman, South Pasadena, both of Calif.

[73] Assignee: City of Hope, Duarte, Calif.

[21] Appl. No.: 199,689

[22] Filed: Feb. 22, 1994

[51] Int. Cl.⁶ ............................................. A61B 5/0452
[52] U.S. Cl. .................................................. 128/703
[58] Field of Search ......................... 128/702, 703, 705

[56] References Cited

PUBLICATIONS

"What is Heart Spectrum Rate Analysis?", *Medic Monitor News*, vol. 2, No. 2, Fall 1993.
A. Davis et al., *Neurocardiology of Arrhythmia and Sudden Cardiac Death*, vol. 20, No. 3, 158–169 (1993).
J. Sarma et al., *PACE*, vol. 10, 485–491 (1987).
J. Ong et al., *American Heart Journal*, vol. 125, No. 3, 744–752 (1993).
J. Sarma et al., *Br. Heart J.*, 60:434–439 (1988).
J. Sarma et al., *Am. J. Cardiol.*, 54:103–108 (1984).
Sarma et al., "Circadian and Power Spectral Changes in Heart Rate and QT Interval During Acute Hypothyroidism: Possible Antiarrhythmic Mechanisms", *PACE*, vol. 16, Pt. II, Abstract No. 120, p. 879 (1993).
J. Sarma, "Circadian and Spectral Changes of RR and QT", *Am. J. Cardiology*, In Press (1994).
M. Antimisiaris et al., "Effects of Amiodarone on the Circadian Rhythm and Power Spectral Changes of Heart Rate and QT Interval", *American Heart Journal*, In Press (1994).
J. Sarm et al., *Am. J. Cardiol.*, 66:959–963 (1990).
J. Sarma et al., "The Concept of Corrected QT Interval", Ch. 3 in *Clinical Aspects of Ventricular Repolarization*, ed. G. Butrous et al., Farrand Press (London 1989).
J. Sarma et al., "Circadian Rhythmicity of Heart Rate and Myocardial Repolarization", Ch. 31 in *Electropharmacological Control of Cardiac Arrhythmias*, eds. Singh et al., Futura Publ. Co. Inc. (Mount Kisco 1994).

*Primary Examiner*—William E. Kamm
*Attorney, Agent, or Firm*—Rothwell, Figg, Ernst & Kurz

[57] ABSTRACT

Apparatus and method for testing the autonomic nervous system of a mammal through bi-variate analysis of heart period (RR) and QT interval variability obtained through data processing of electrocardiographic data. The method and apparatus enables both the parasympathetic and sympathetic controls on the heart to be evaluated for imbalances therebetween, which may indicate a predisposition for sudden cardiac death.

18 Claims, 7 Drawing Sheets

AUTONOMIC NERVOUS SYSTEM TESTING BY BI-VARIATE SPECTRAL ANALYSIS OF HEART PERIOD AND QT INTERVAL VARIABILITY

BACKGROUND OF THE INVENTION

1. Field of the Invention

This invention relates generally to methods of patient diagnosis through processing of electrocardiogram (ECG) data, and particularly to methods and apparatus for evaluating the autonomic nervous system control of the heart through novel processing of ECG data.

2. Description of Background Art

The cardiovascular system responds to various demands of the body under control of the autonomic nervous system, which consists of the parasympathetic and sympathetic limbs. Certain pathologic conditions such as diabetic autonomic neuropathy and post-myocardial infarction can impair the autonomic control of the heart, which could result in various arrhythmias such as ventricular fibrillation, ventricular tachycardia, sinus bradycardia, atrioventricular block, and sudden asystole, among others. An imbalance between the sympathetic autonomic control and the parasympathetic autonomic control may predispose a patient to sudden cardiac death.

A conventional practice for evaluation of the autonomic nervous system control of the heart is the study of heart period variability (in both the time and frequency domains) under various conditions of autonomic stimulation including deep breathing, exercise, rest, mental and pharmacological stress testing, and various other autonomic maneuvers. However, clinical data has shown that heart period variability is predominantly representative of parasympathetic tone only, and that the ratio of low to high frequency spectral power of heart rate variability is not always reliable as a measure of sympathetic autonomic activity. As a result, analysis of heart period variability alone cannot detect adequately imbalances between the parasympathetic and sympathetic autonomic controls of the heart. Furthermore, heart rate variability cannot directly reflect ventricular response to autonomic stimuli, which may be a critical determinant of the susceptibility of a patient to ventricular arrhythmias and sudden cardiac death.

SUMMARY OF THE INVENTION

The present invention overcomes the deficiencies in the conventional autonomic evaluation by providing a novel method and apparatus for distinguishing between the parasympathetic and sympathetic control inputs to the heart. The present invention thus provides the cardiologist with a direct method for evaluating imbalances between the parasympathetic and sympathetic controls of the autonomic nervous system.

The present invention is based on the discovery by the present inventors that the variability of the QT interval of the heart activity wave is a direct indicator of sympathetic autonomic control of the heart, and thus QT interval variability complements heart period (RR) variability for a complete evaluation of the autonomic nervous system control of the heart. The present invention provides a method and apparatus for analyzing the QT interval variability simultaneously with the heart period (RR) variability. Through such simultaneous analysis, it becomes possible for the first time to better identify patients with autonomic imbalance.

In particular, the present invention provides a method for testing the autonomic nervous system of a mammal, comprising the steps of obtaining electrocardiographic (ECG) data from the mammal under a selectable state of autonomic stimulation for a predetermined period of time; calculating heart period (RR) intervals and QT intervals for a predetermined number of normally conducted heart beats represented in the ECG data, and outputting the calculated RR and QT intervals in the form of electrical data signals; calculating power spectral densities of the RR and QT intervals; and analyzing the calculated RR and QT interval power spectral densities with respect to each other as an indication of the state of balance between parasympathetic and sympathetic controls of the autonomic nervous system of the mammal. In another aspect, the present invention further provides apparatus for testing the autonomic nervous system of a mammal.

BRIEF DESCRIPTION OF THE DRAWINGS

The present invention will become more fully understood from the detailed description given hereinbelow in conjunction with the accompanying drawings, which are given by way of illustration only and are not limitative of the present invention, and wherein.

DETAILED DESCRIPTION OF THE PREFERRED EMBODIMENT

Figure 1:
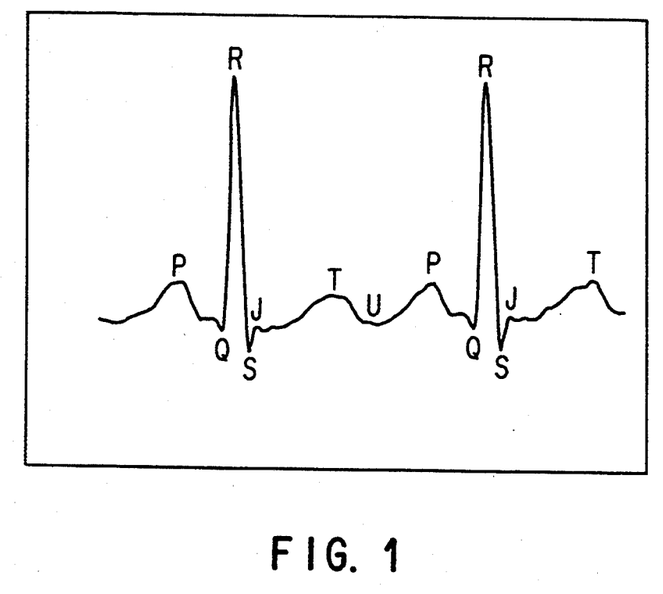
FIG. 1 is a graphic representation of a typical electrocardiograph (ECG) tracing with normal cardiac activation.

FIG. 1 illustrates a typical ECG tracing for a healthy individual. The letters P, Q, R, S, T and U refer to the conventional labelling of different waves during one complete cardiac cycle. The U wave is usually not present in healthy individuals. The letter J refers to the point where the slope of the terminal portion of the S wave abruptly changes toward the horizontal axis, and marks the beginning of the ST segment of the cardiac cycle. Under conditions of normal cardiac activation the R wave represents the conducted sinus beat of the heart, and the interval between the apexes of consecutive R waves represents the heart period in units of time, with the heart rate being the reciprocal of the RR interval expressed as beats per minute.

The QT interval is conventionally measured from the beginning of the Q wave to the end of the T wave (also known as QeT), or from the beginning of the Q wave to the apex of the T wave (also known as QaT). The end of the T wave is approximated by performing a linear regression analysis on the points in the steepest segment of the terminal portion of the T wave, and finding the intersection of the resultant regression line with the isoelectric line (not shown) of the electrocardiogram. Prior to the present invention, the normalized QT interval (QTc), normalized using Bazett's formula, was typically evaluated for prolongation, because an abnormally prolonged QTc interval under certain disease conditions is associated with a risk of sudden cardiac death.

Figure 6A:
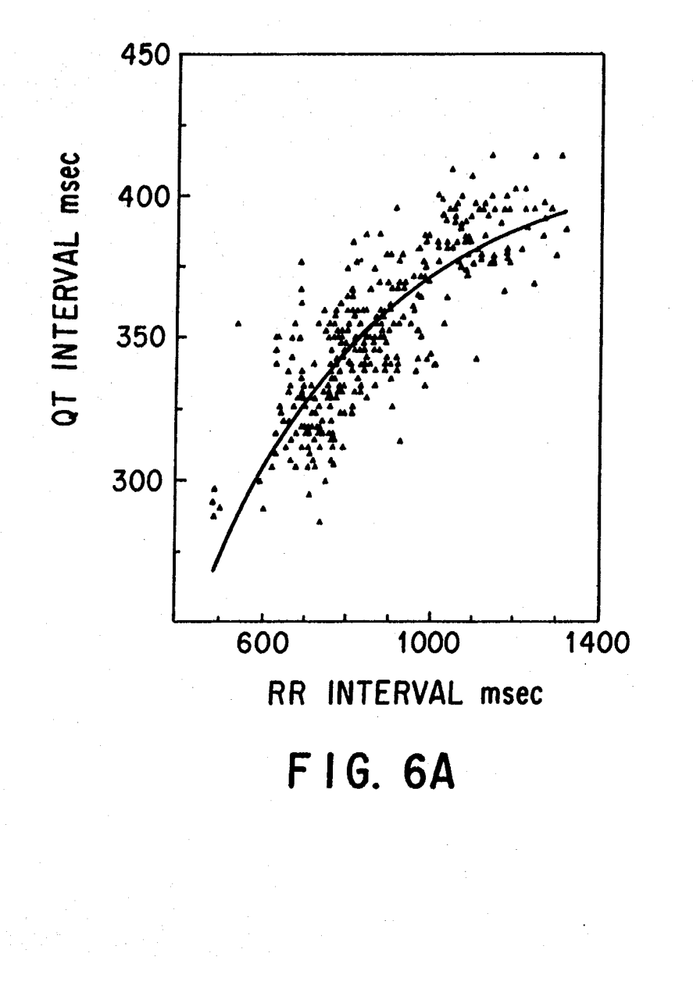
FIGS. 6A and 6B are graphs illustrating the relationship between corresponding QT and RR intervals as measured, and as normalized QT for a predetermined value of RR.
Figure 6B:
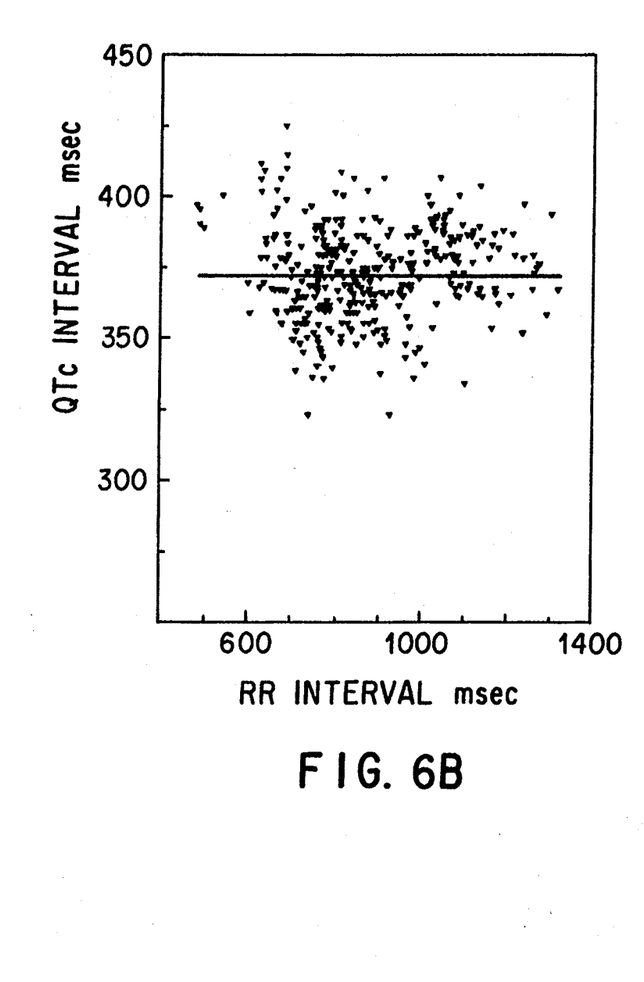

In the present invention, the QT interval is normalized differently, since the QT interval often exhibits an exponential relationship to the RR interval, as shown in the graph of FIG. 6A. The solid exponential curve was obtained by fitting the data points of QT intervals plotted against corresponding RR intervals, measured every 5 minutes over a 24 hour period, with an exponential function through nonlinear regression analysis. The corresponding values of the exponential curve were subtracted from each data point and the value of the QT interval corresponding to RR=1000 msec on the curve was then added to resulting array of data points to obtain the heart rate normalized (corrected) QT interval, QTc, which is plotted against RR in the graph of FIG. 6B. Note that QTc is independent of RR, as the data points are randomly scattered above and below a line parallel to the horizontal axis. During autonomic manipulation over a short period, usually a few minutes, the QT interval may not exhibit a clear relationship to the RR interval. Under such conditions QT normalization is not needed.

Figure 2:
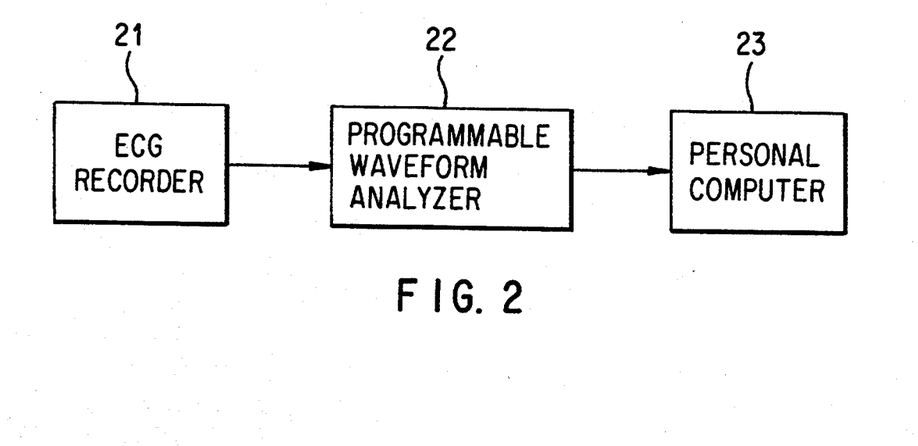
FIG. 2 is a block diagram of apparatus for carrying out the improved method according to one embodiment of the present invention.

FIG. 2 illustrates one embodiment of apparatus for carrying out the bi-variate spectral analysis according to the present invention. Electrocardiograms are recorded by an ECG recorder 21, via electrical leads placed on the subject. The ECG recorder 21 may be a magnetic tape FM recorder/player such as for example Hewlett Packard Model 3964A connected to the subject through an ECG amplifier, or any equivalent thereof for short-term tests, or a 24 hour ambulatory electrocardiographic recorder for circadian data evaluation.

The recorded electrocardiograms are outputted by the recorder 21 into a programmable waveform analyzer 22, which may be implemented by a Norland 3001 Programmable Waveform Analyzer or any equivalent thereof. For electrocardiograms recorded on a 24 hour ambulatory recorder, the recorded ECG data may be outputted into the waveform analyzer at 240 times recording speed using a Holter scanning system. ECG data recorded on the FM tape recorder may be outputted at the original recording speed.

The recorded ECG data is processed in the waveform analyzer 22 to acquire RR and QT interval data, and the acquired RR and QT interval data is then outputted from the waveform analyzer into a host personal computer 23, which may be an IBM-compatible personal computer or any equivalent thereof, over a suitable communication bus. The measured RR and QT interval data is processed and analyzed in the computer 23, and outputted in the form of high resolution graphics or statistical data.

The data acquisition and processing in the waveform analyzer and computer will now be described in detail with reference to the diagrams of FIGS. 3 and 4. However, it will be recognized that the data acquisition and analysis of the RR and QT intervals can be integrated into a single dedicated system based on a high performance computer platform with data acquisition hardware and software, without the need for a waveform analyzer.

Figure 3:
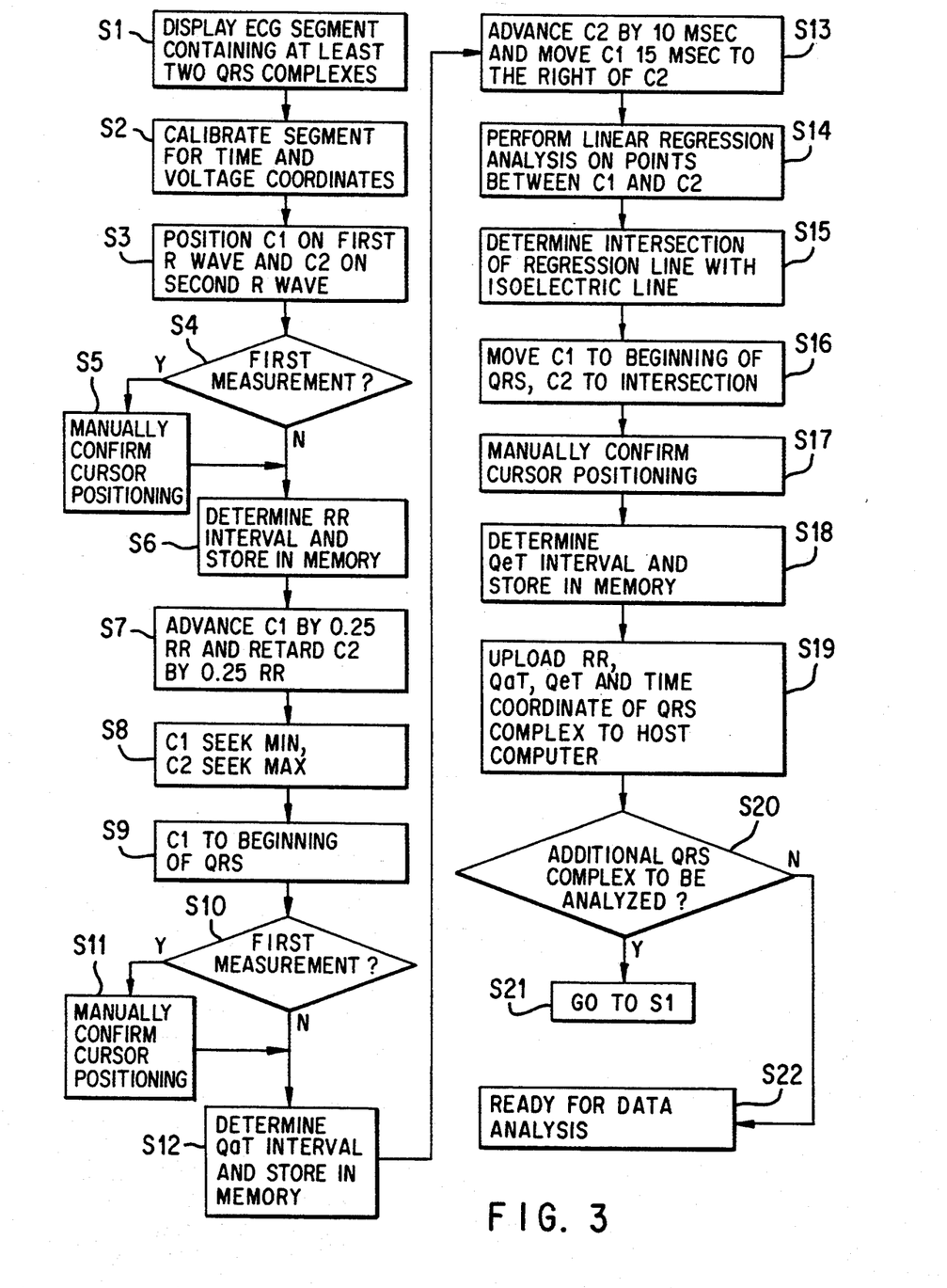
FIG. 3 is a flow chart diagram of the processing steps for data acquisition according to one embodiment of the present invention.
Figure 4:
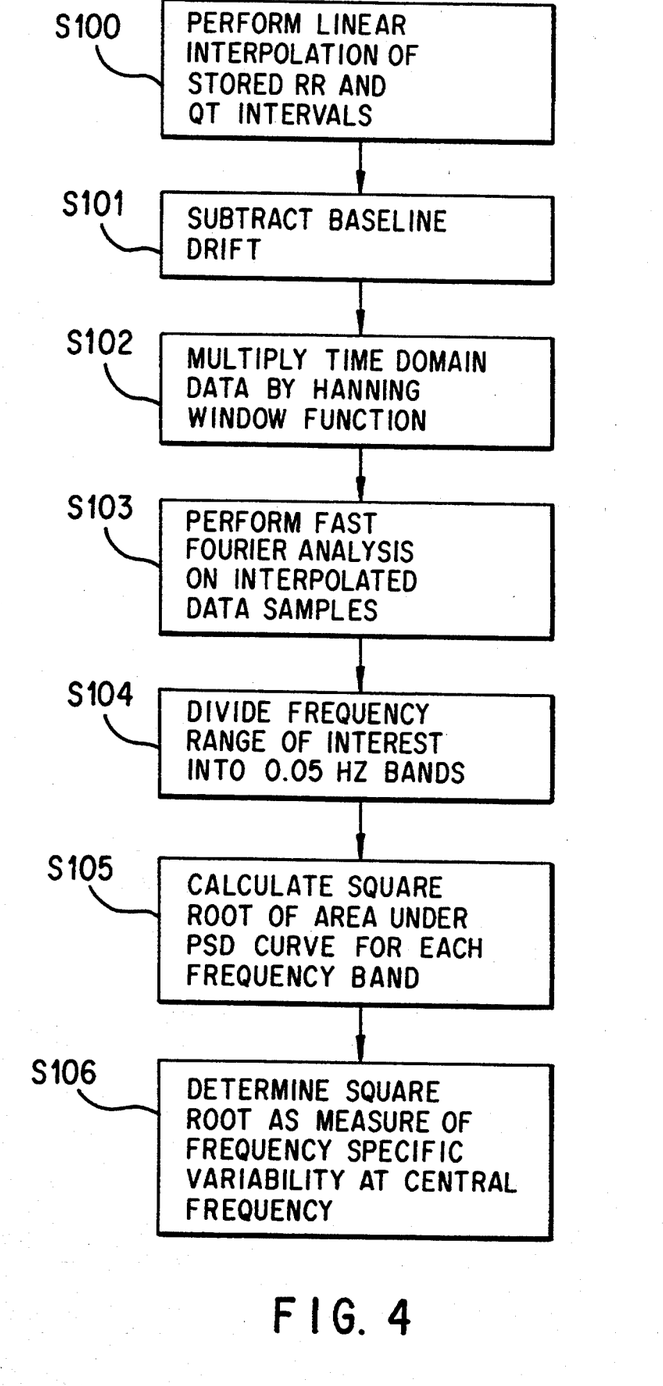
FIG. 4 is a flow chart diagram of the processing steps for data analysis according to one embodiment of the present invention.

Referring to FIG. 3, the waveform analyzer digitizes incoming ECG data and holds a predetermined length of the ECG in memory. At step S1, a segment of the ECG waveform containing at least two QRS complexes is displayed on the display screen of the waveform analyzer, with the first R wave positioned at the left of the display screen ⅛ the distance of the screen trace from the edge of the screen display. In addition to stored data the displayed data can be from a direct analog input to the analyzer. At step S2 the segment is calibrated by entering the time and voltage coordinates of the first QRS complex into memory registers of the analyzer.

The waveform analyzer has two movable cursors, c1 and c2, which are visible on the display screen and which can be moved via programming to seek various characteristic points on the displayed ECG waveform signal. At step S3, the first cursor c1 is moved to the apex of the first R wave and the second cursor c2 is positioned at the apex of the second R wave, through peak voltage level detection. At step S4 it is determined whether the current measurement is the first measurement for the particular ECG being processed. If so, the program pauses at step S5 to allow the user to visually observe the cursor positioning and either confirm the accuracy thereof or manually adjust the cursor position to the desired locations through the keyboard of the analyzer. If so adjusted, the positions and voltage levels will be memorized for calibration of subsequent measurements. At step S6, the RR interval in msec is determined as the distance between the cursors c1 and c2, and is stored in a memory register of the analyzer. At step S7, the c1 cursor is advanced (i.e., moved to the right) by 0.25 times the measured RR interval, and c2 is retarded (i.e., moved to the left) by the same distance. At this time, referencing FIG. 1, c1 and c2 are located on either side of the T wave between the adjacent R waves. At step S8, a seek command is issued for c1 to seek the minimum voltage point and for c2 to seek the maximum voltage point between the two cursors. Thus, c2 will now be positioned at the apex of the T wave (appropriate modification of the seek command is made in the case of inverted T waves). At step S9, c1 is moved to the beginning coordinates of the QRS complex as stored in memory. Similar to steps S4 and S5, steps S10 and S11 enable the user to visually and manually confirm or adjust the proper positioning of the cursors for the first measurement. At step S12, the distance between c1 and c2 is calculated to determine the QaT interval, and this interval is stored in a memory register.

At step S13, c2 is advanced to the right by 10 milliseconds and c1 is moved to a location 15 milliseconds to the right of c2, so that c1 and c2 are now positioned on the steepest segment of the terminal portion of the T wave. Appropriate adjustments can be made in the event of abnormal T waves. Next, at step S14, a linear regression is performed on the points between c1 and c2 to obtain a fitted regression line through such points. At step S15 the intersection of the regression line with the isoelectric line of the ECG signal is determined. The isoelectric line is determined by the voltage level at the beginning of the QRS complex (PQ segment). This intersection point is then taken as the termination point of the T wave.

At step S16, c1 is moved back to the beginning of the QRS complex, and c2 is moved to the intersection point. At step S17, the user visually confirms the positioning of the cursors and manually adjusts the positions if necessary. At step S18, the QeT interval is determined by calculating the distance between c1 and c2, and is stored in memory. Next, as represented at step S19, the measured RR, QaT, QeT, and initial time coordinates of the QRS complex are uploaded to the host computer 23, by issuing an interrupt over the bus connecting the waveform analyzer to the computer. The computer then receives the data values and places them into appropriate arrays in memory for further processing. At step S20, it is determined whether additional QRS complexes exist in the ECG waveform for processing. If so, the program resets to step S1 (step S21) and repeats the data acquisition procedure for the next QRS complex. If not, at step S22, the waveform analyzer communicates the completion of data acquisition to the computer 23, indicating that analysis of the data in the computer may begin. For subsequent measurements, the data acquisition program will pause for user confirmation only if the new measurement differs from the previous measurement by a predetermined percentage. This provides a means of rejecting non-sinus beats and the two or three immediately following beats.

Data processing in the computer 23 will now be explained with reference to FIG. 4. At step S100, the acquired RR and QT interval values stored in an array in the computer 23 are linearly interpolated to obtain samples equally spaced in time. At step S101, the data is smoothed by subtracting for baseline drift, and at step S102 the time domain RR and QT interval data is multiplied by a Hanning window function in order to minimize spectral leakage. At step S103, the evenly spaced linearly interpolated data samples are subjected to fast Fourier analysis to obtain frequency power spectra of the RR and QT intervals (either of the QaT or QeT calculated intervals may be used selectively). Preferably, the power spectra are calculated from more than 64 consecutive sinus beats. The lowest frequency capable of being studied is dependent on the total time duration of the data samples, while the highest frequency depends on the sampling interval. Thus, the total duration of the ECG used for power spectral analysis should contain at least 3 cycle lengths corresponding to the lowest frequency of interest, and at least 5 samples should exist within one cycle length of the highest frequency of interest.

At step S104, the frequency range of interest from the frequency domain data obtained through the fast Fourier analysis is divided into bands of 0.05 Hz each. At step S105 the square root of the area under the power spectral density (PSD) curves within each 0.05 Hz band is calculated, and at step S106 the square root is determined as a measure of the frequency specific variability at the determined central frequency.

Figure 5A:
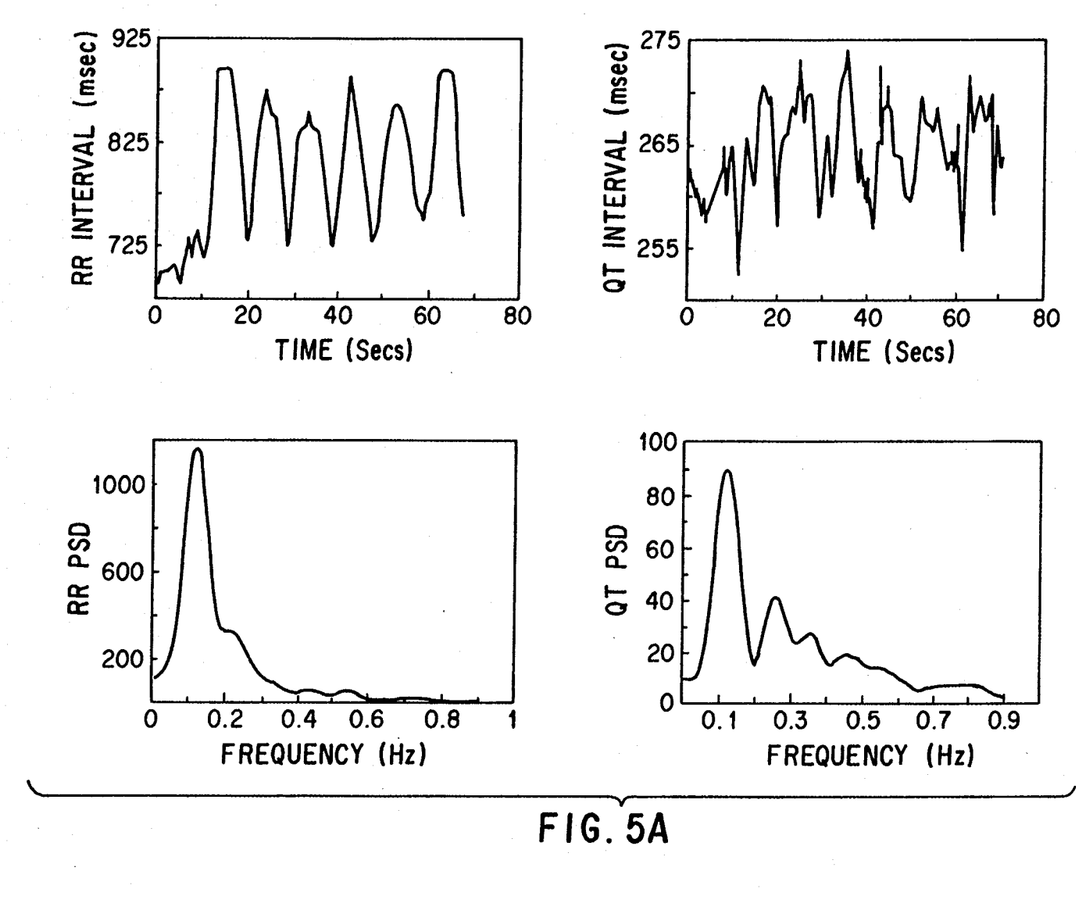
FIGS. 5A and 5B are graphs of the obtained RR and QT interval variabilities in the time and frequency domains for a normal subject and a pathological subject, respectively.
Figure 5B:
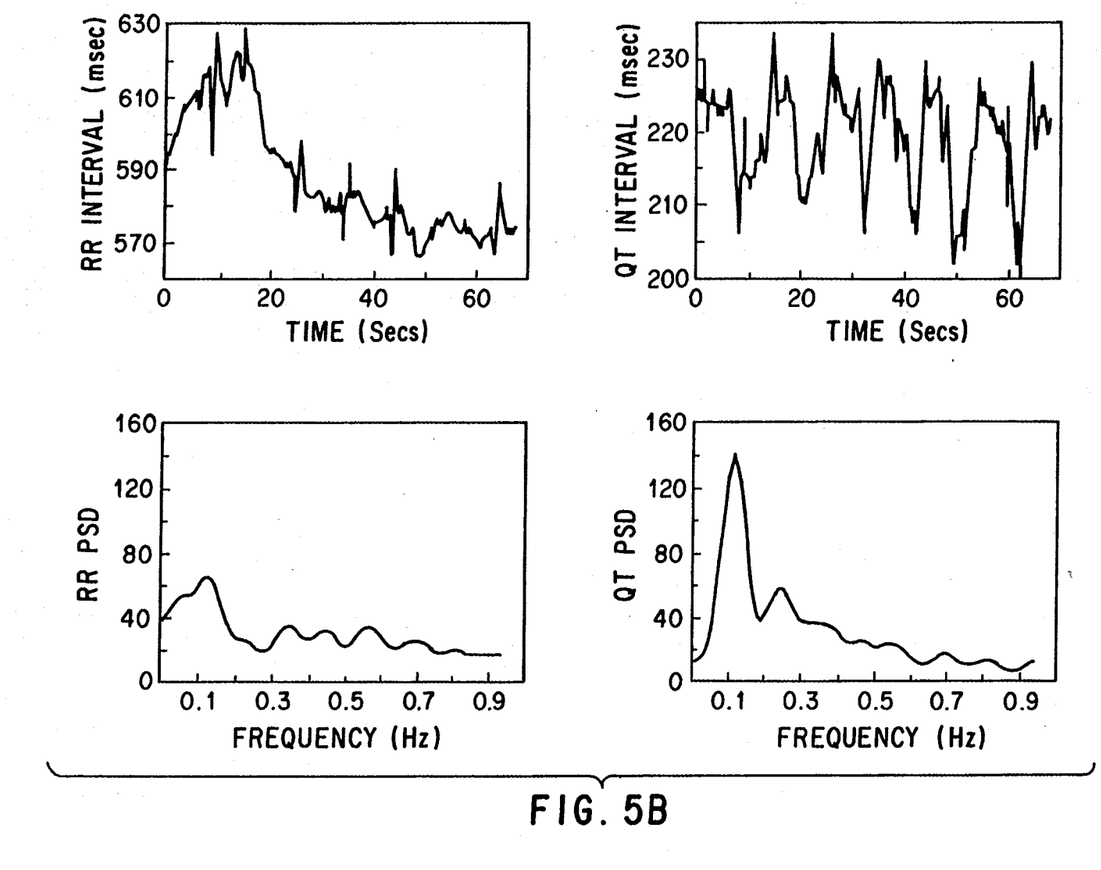

FIGS. 5A and 5B illustrate graphs representing the time and frequency domain data of the measured RR and QT interval variability in units of milliseconds and voltage level, respectively. The graphics representation can be generated using commercially available graphics software such as Stanford Graphics Software or its equivalent. The processed frequency spectra data can be transferred to statistical format files such as Lotus files to facilitate statistical analysis and imported to the graphics software from the Lotus files.

The obtained power spectral densities of the RR and QT intervals as shown in FIGS. 5A and 5B are analyzed for coherence, relative phase and gain. The spectral coherence is a measure of the linear association between the RR and QT variables at various frequencies. FIG. 5A shows time and frequency domain RR and QT data obtained from a normal subject during a deep breathing autonomic maneuver. The RR PSD peak is several times larger than the QT PSD peak. In contrast, FIG. 5B shows the time and frequency domain RR and QT data for a subject with diabetic autonomic neuropathy (DAN). While the subject exhibits a reduced heart period variability (note that the RR PSD peak is abnormally small), the QT PSD peak is normal. Thus, the spectral power ratio between the RR interval and the QT interval is very small, suggesting a severe autonomic imbalance between the parasympathetic and sympathetic controls on the heart which may predispose the patient to sudden cardiac death, which is common among DAN patients.

Figure 7A:
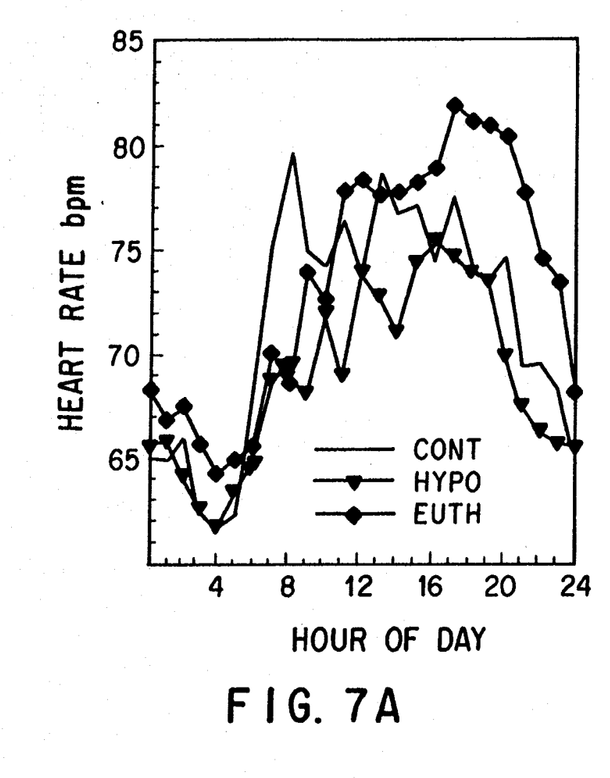
FIGS. 7A and 7B are graphs illustrating circadian variations of heart rate and normalized QT intervals for control subjects and pathological subjects before and after treatment.
Figure 7B:
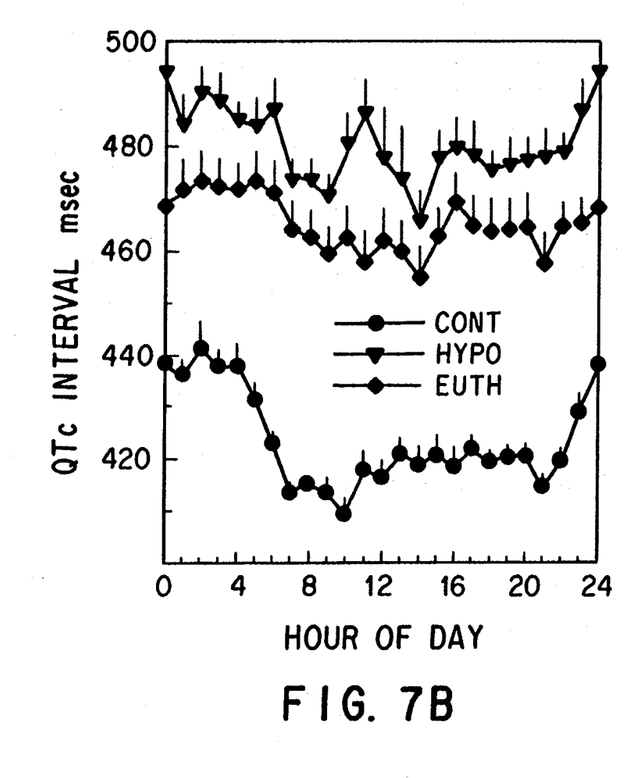

FIGS. 7A and 7B illustrate changes in circadian patterns of heart rate (A) and QTc (rate-normalized QT) interval (B) in hypothyroid patients before treatment (HYPO) and after treatment under euthyroid conditions (EUTH). The heart rate in beats per minute is computed as the inverse of the RR interval, expressed in minutes. The circadian pattern of a healthy control subject (CONT) is also presented for comparison. The data points represent hourly mean values. As shown in the graph, after treatment the heart rate became almost normal; however, QTc was only moderately shortened after treatment, being still substantially prolonged as compared to the normal control QTc.

The RR and QT interval variability analysis of the present invention can be performed on electrocardiogram data recorded under many different conditions of autonomic stimulation, including rest, exercise, post-exercise, mental stress testing, pharmacological stress testing, ambulatory electrocardiography, tilt-table testing, programmed breathing, valsalva maneuver, cold presser testing, hyperventilation, sustained hand grip, face immersion, and drug intervention for directly or indirectly affecting the autonomic nervous system or cardiac repolarization. Patient groups likely to benefit from the present invention include patients with coronary artery disease, heart failure, diabetes, long QT syndrome, hypertension, unexplained syncope, or neurological disorders. As will be recognized from the above description, the present invention provides a novel technique for evaluating the autonomic system to detect imbalances between the parasympathetic and sympathetic controls of the cardiac function, which heretofore has not been possible.

The invention having been thus described, it be apparent to those skilled in the art that the same may be varied in many ways without departing from the spirit and scope of the invention. Accordingly, any and all such modifications are intended to be covered by the following claims.

What is claimed is:

1. A method for testing the autonomic nervous system of a mammal, comprising the steps of:
    obtaining electrocardiographic (ECG) data from said mammal under a selectable state of autonomic stimulation for a predetermined period of time;

calculating heart period (RR) intervals and QT intervals for a predetermined number of heart beats represented in said ECG data, and outputting the calculated RR and QT intervals in the form of electrical data signals;

calculating power spectral densities of said RR and QT intervals; and analyzing the calculated RR and QT interval power spectral densities with respect to each other as an indication of the state of balance between parasympathetic and sympathetic controls of the autonomic nervous system of said mammal.

2. A method for testing the autonomic nervous system of a mammal as set forth in claim 1, wherein the step of calculating RR and QT intervals comprises the step of measuring QT intervals from the beginning of a QRS complex in said ECG data to the apex of a succeeding T wave.

3. A method for testing the autonomic nervous system of a mammal as set forth in claim 1, wherein the step of calculating RR and QT intervals comprises the step of measuring QT intervals from the beginning of a QRS complex in said ECG data to the terminal portion of a succeeding T wave in said ECG data.

4. A method for testing the autonomic nervous system of a mammal as set forth in claim 3, further comprising the step of calculating said terminal portion of said T wave through linear regression analysis.

5. A method for testing the autonomic nervous system of a mammal as set forth in claim 1, wherein the step of calculating power spectral densities comprises the step of performing fast Fourier analysis on said calculated RR and QT intervals.

6. A method for testing the autonomic nervous system of a mammal, comprising the steps of:

obtaining electrocardiographic (ECG) data from said mammal under a selectable state of autonomic stimulation for a predetermined period of time;

calculating heart period (RR) intervals and QT intervals for a predetermined number of heart beats represented in said ECG data, and outputting the calculated RR and QT intervals in the form of electrical data signals; and analyzing the calculated RR and QT intervals with respect to each other as an indication of the state of balance between parasympathetic and sympathetic controls of the autonomic nervous system of said mammal.

7. A method for testing the autonomic nervous system of a mammal as set forth in claim 6, wherein said predetermined period of time comprises a 24 hour period, and said step of analyzing comprises the steps of outputting said electrical data signals in the form of circadian patterns and performing analysis of circadian variation of said calculated RR and QT intervals with respect to each other.

8. A method for testing the autonomic nervous system of a mammal as set forth in claim 6, wherein the step of calculating RR and QT intervals comprises the step of measuring QT intervals from the beginning of a QRS complex in said ECG data to the apex of a succeeding T wave.

9. A method for testing the autonomic nervous system of a mammal as set forth in claim 6, wherein the step of calculating RR and QT intervals comprises the step of measuring QT intervals from the beginning of a QRS complex in said ECG data to the terminal portion of a succeeding T wave in said ECG data.

10. Apparatus for testing the autonomic nervous system of a mammal, comprising:

means for obtaining electrocardiographic (ECG) data from said mammal under a selectable state of autonomic stimulation for a predetermined period of time;

means for calculating heart period (RR) intervals and QT intervals for a predetermined number of heart beats represented in said ECG data, and for outputting the calculated RR and QT intervals in the form of electrical data signals;

means for calculating power spectral densities of said RR and QT intervals; and means for analyzing the calculated RR and QT interval power spectral densities with respect to each other as an indication of the state of balance between parasympathetic and sympathetic controls of the autonomic nervous system of said mammal.

11. Apparatus for testing the autonomic nervous system of a mammal as set forth in claim 10, wherein said means for calculating RR and QT intervals measures QT intervals from the beginning of a QRS complex in said ECG data to the apex of a succeeding T wave.

12. Apparatus for testing the autonomic nervous system of a mammal as set forth in claim 10, wherein said means for calculating RR and QT intervals measures QT intervals from the beginning of a QRS complex in said ECG data to the terminal portion of a succeeding T wave in said ECG data.

13. Apparatus for testing the autonomic nervous system of a mammal as set forth in claim 12, further comprising means for calculating said terminal portion of said T wave through linear regression analysis.

14. Apparatus for testing the autonomic nervous system of a mammal as set forth in claim 10, wherein said means for calculating power spectral densities comprises means for performing fast Fourier analysis on said calculated RR and QT intervals.

15. Apparatus for testing the autonomic nervous system of a mammal as set forth in claim 10, wherein said means for obtaining electrocardiographic (ECG) data comprises a magnetic tape recorder/player.

16. Apparatus for testing the autonomic nervous system of a mammal as set forth in claim 10, wherein said means for obtaining electrocardiographic (ECG) data comprises a 24 hour ambulatory ECG recorder.

17. Apparatus for testing the autonomic nervous system of a mammal as set forth in claim 10, wherein said means for calculating heart period (RR) intervals and QT intervals comprises a waveform analyzer.

18. Apparatus for testing the autonomic nervous system of a mammal as set forth in claim 10, wherein said means for calculating power spectral densities of said RR and QT intervals comprises a programmed personal computer.

* * * * *